US010828035B2

(12) United States Patent
Maekubo

(10) Patent No.: US 10,828,035 B2
(45) Date of Patent: Nov. 10, 2020

(54) CONNECTOR, MEDICAL CLIP DEVICE AND METHOD FOR PRODUCING MEDICAL CLIP DEVICE

(71) Applicant: KANEKA CORPORATION, Osaka (JP)

(72) Inventor: Naotake Maekubo, Okaya (JP)

(73) Assignee: KANEKA CORPORATION, Osaka (JP)

(*) Notice: Subject to any disclaimer, the term of this patent is extended or adjusted under 35 U.S.C. 154(b) by 162 days.

(21) Appl. No.: 15/780,151

(22) PCT Filed: Dec. 6, 2016

(86) PCT No.: PCT/JP2016/086143
§ 371 (c)(1),
(2) Date: May 30, 2018

(87) PCT Pub. No.: WO2017/104475
PCT Pub. Date: Jun. 22, 2017

(65) Prior Publication Data
US 2018/0353183 A1    Dec. 13, 2018

(30) Foreign Application Priority Data

Dec. 18, 2015    (JP) .................................. 2015-247414

(51) Int. Cl.
*A61B 17/10* (2006.01)
*A61B 17/122* (2006.01)
(Continued)

(52) U.S. Cl.
CPC ........ *A61B 17/10* (2013.01); *A61B 17/00234* (2013.01); *A61B 17/083* (2013.01);
(Continued)

(58) Field of Classification Search
CPC . A61B 17/10; A61B 17/1285; A61B 17/1227; A61B 17/083; A61B 17/00234;
(Continued)

(56) References Cited

U.S. PATENT DOCUMENTS 3,958,576 A * 5/1976 Komiya ............... A61B 17/083
606/142
6,402,765 B1    6/2002 Monassevitch et al.
(Continued)

FOREIGN PATENT DOCUMENTS

JP    2004-503276 A    2/2004
JP    2007-275542    * 10/2007 ............. A61B 17/28
(Continued)

OTHER PUBLICATIONS

International Search Report for PCT/JP2016/086143 (PCT/ISA/210) dated Mar. 14, 2017.
(Continued)

*Primary Examiner* — Katherine M Shi
*Assistant Examiner* — Alyssa M Keane
(74) *Attorney, Agent, or Firm* — Birch, Stewart, Kolasch & Birch, LLP

(57) ABSTRACT

An object of the present invention is to provide a connector that facilitates a connecting operation with a clip, prevents an unintended release of the clip, and suppresses a misoperation of the clip in a holding operation; a medical clip device including the connector; and a method for producing the medical clip device. A connector (20) for connecting a medical clip for holding a target site with a line member for moving the clip comprises: a through hole (21) whose depth direction is nonparallel to an axial direction; and a thin part that is formed at least at a part distal to the through hole and is thinner than a distal end of the through hole (21).

12 Claims, 8 Drawing Sheets

(51) Int. Cl.
*A61B 17/128* (2006.01)
*A61B 17/00* (2006.01)
*A61B 17/08* (2006.01)
*A61B 17/29* (2006.01)

(52) U.S. Cl.
CPC ...... *A61B 17/1227* (2013.01); *A61B 17/1285* (2013.01); *A61B 17/29* (2013.01); *A61B 2017/00477* (2013.01); *A61B 2017/00526* (2013.01)

(58) Field of Classification Search
CPC .......... A61B 17/29; A61B 2017/00526; A61B 2017/0047; A61B 17/08
USPC .......................................................... 606/151
See application file for complete search history.

(56) References Cited

U.S. PATENT DOCUMENTS

| 2002/0177859 | A1 | 11/2002 | Monassevitch et al. | |
| 2005/0043757 | A1 | 2/2005 | Arad et al. | |
| 2008/0312665 | A1* | 12/2008 | Shibata | A61B 17/083 |
| | | | | 606/142 |
| 2015/0305741 | A1* | 10/2015 | Satake | A61B 17/122 |
| | | | | 606/142 |

FOREIGN PATENT DOCUMENTS

| JP | 2007-275542 A | 10/2007 |
| JP | 2008-289524 A | 12/2008 |
| JP | 2009-189704 A | 8/2009 |
| JP | 3159939 U | 6/2010 |
| JP | 2013-085860 A | 5/2013 |

OTHER PUBLICATIONS

Written Opinion of the International Searching Authority for PCT/JP2016/086143 (PCT/ISA/237) dated Mar. 14, 2017.
Japanese Notice of Reasons for Refusal (including an English translation thereof) issued in the corresponding Japanese Patent Application No. 2017-555991 dated Apr. 28, 2020.

* cited by examiner

[Fig. 1]
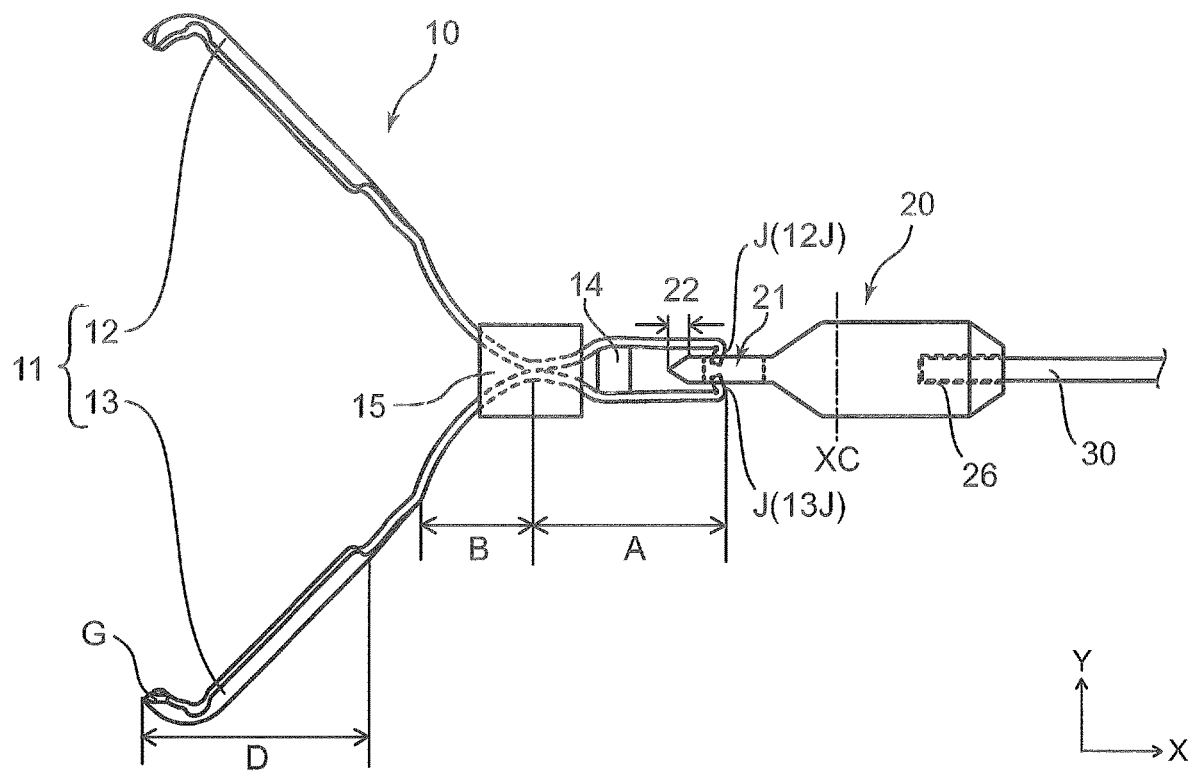
[Fig. 3]
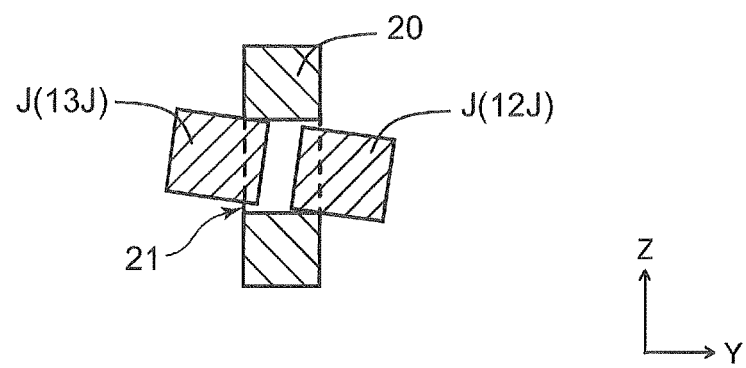

[Fig. 2]
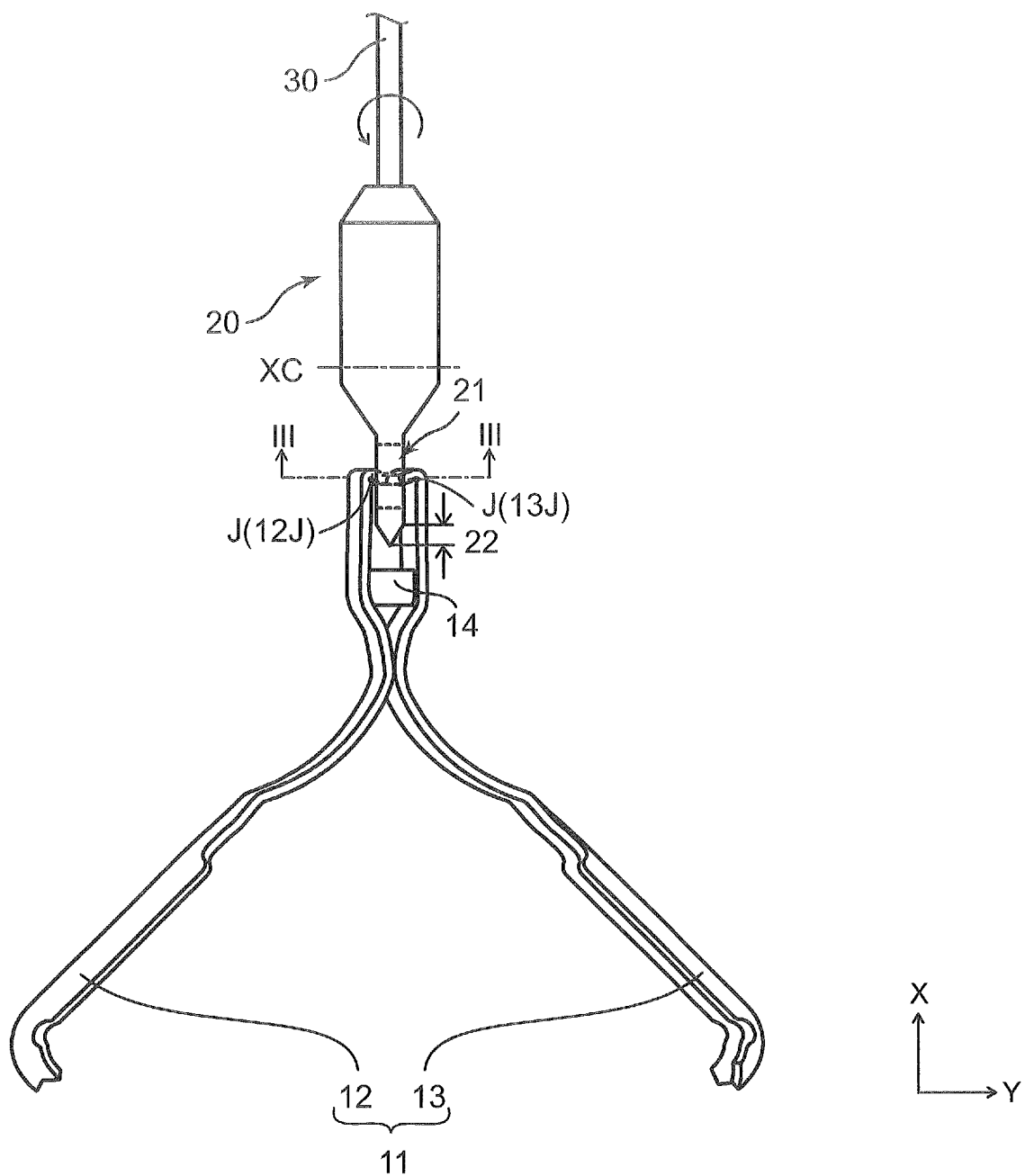

[Fig. 4]
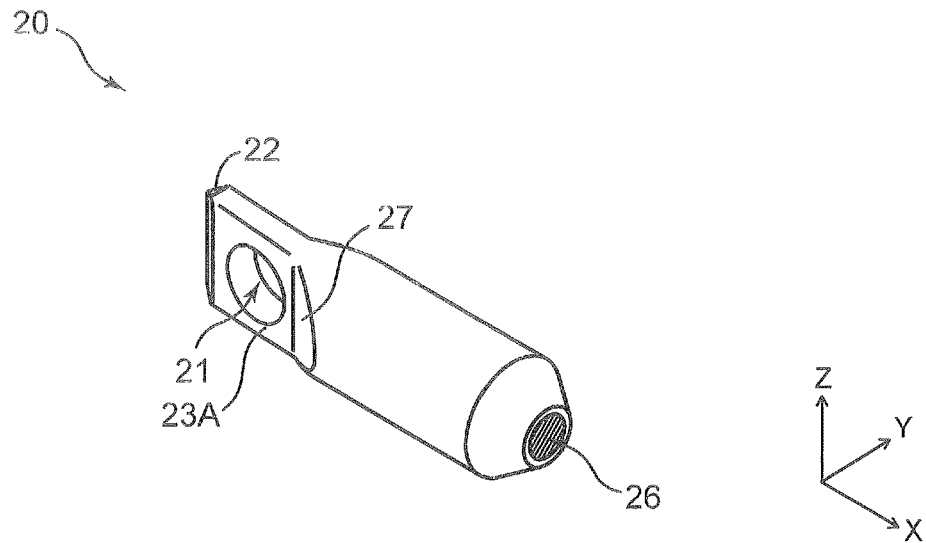
[Fig. 5]
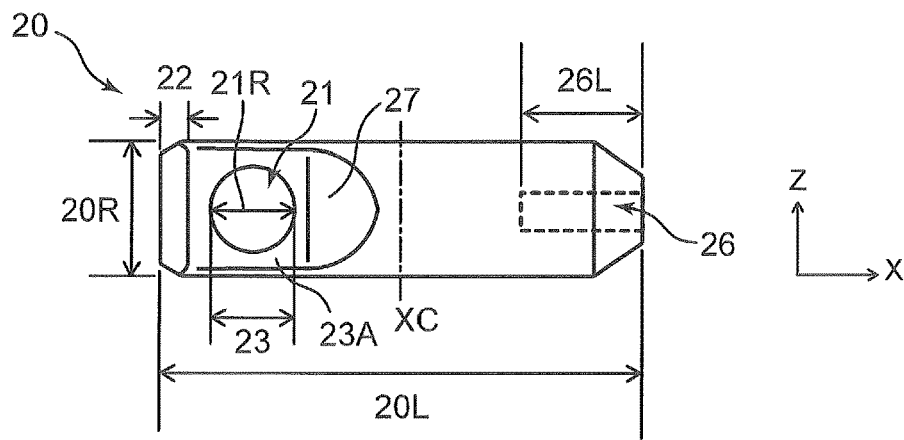
[Fig. 6]
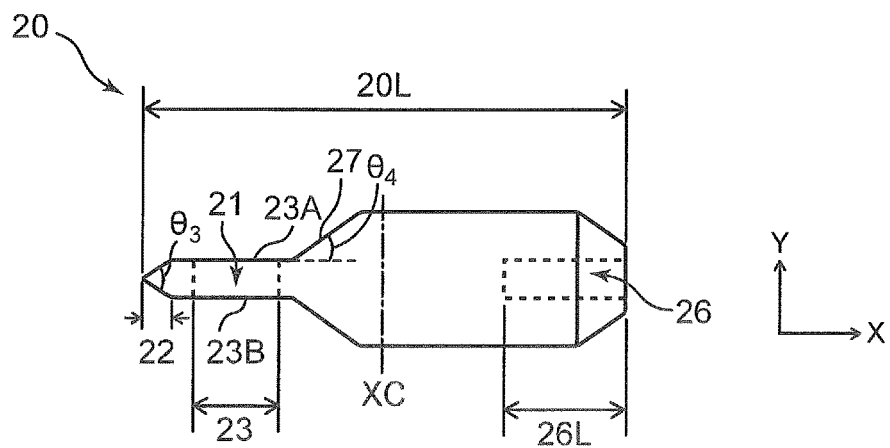

[Fig. 7]
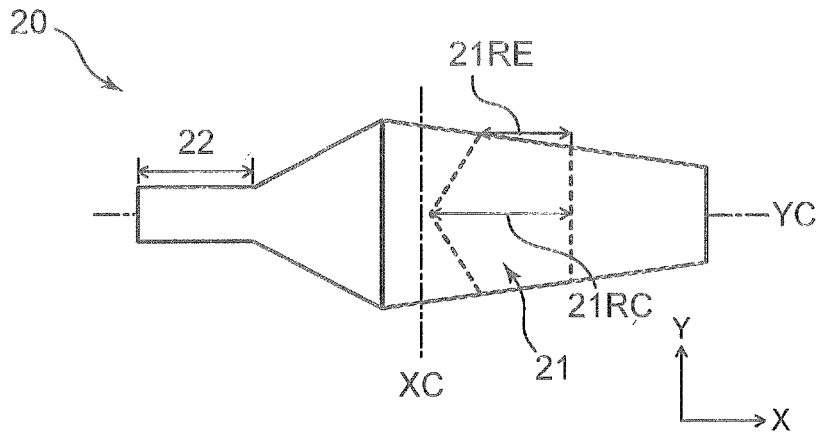
[Fig. 8]
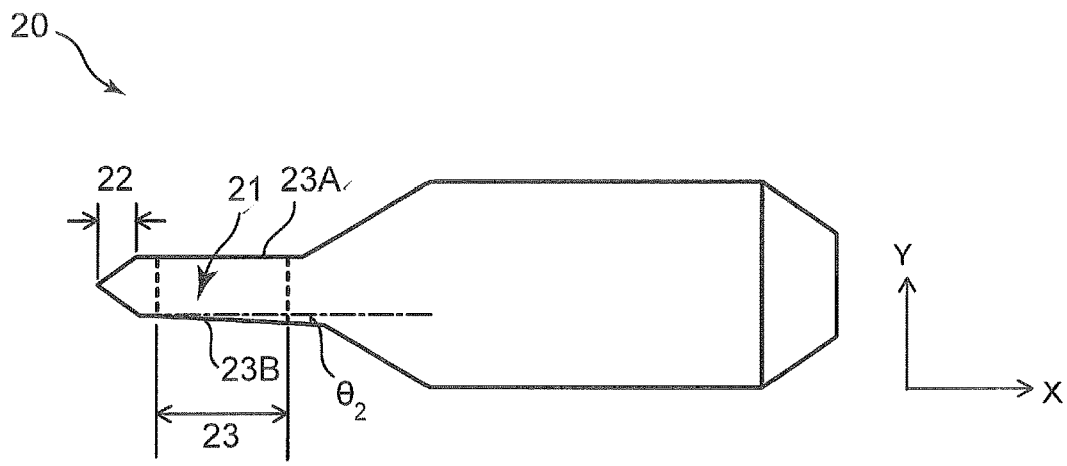
[Fig. 9]
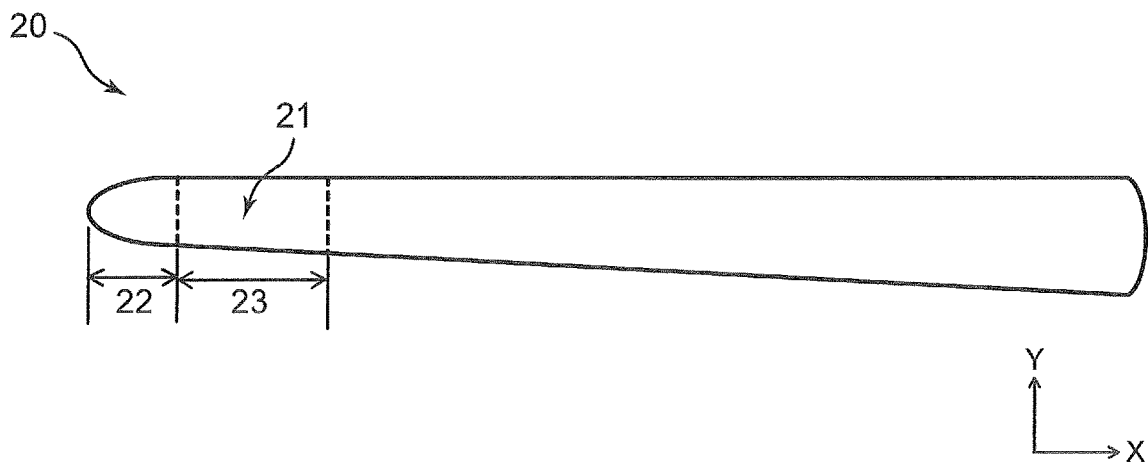

[Fig. 10]
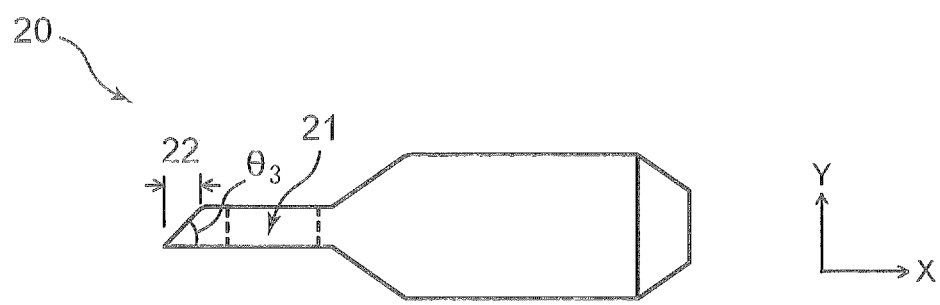
[Fig. 11]
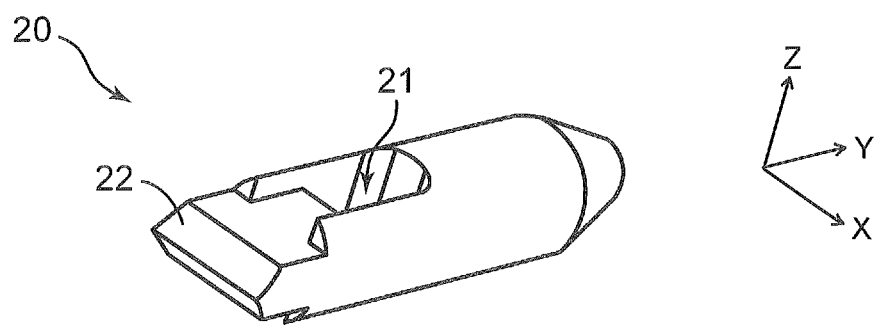

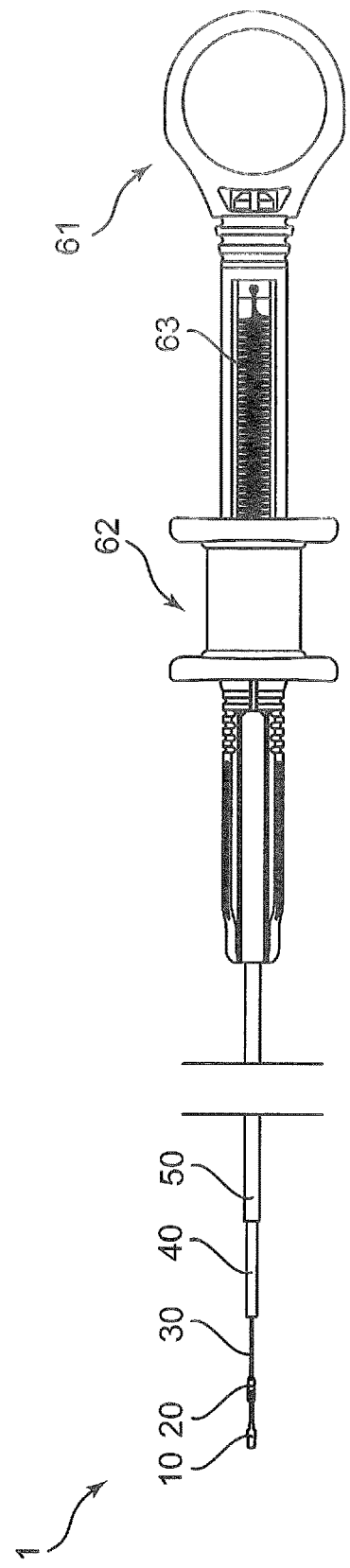
[Fig. 12]

[Fig. 13]
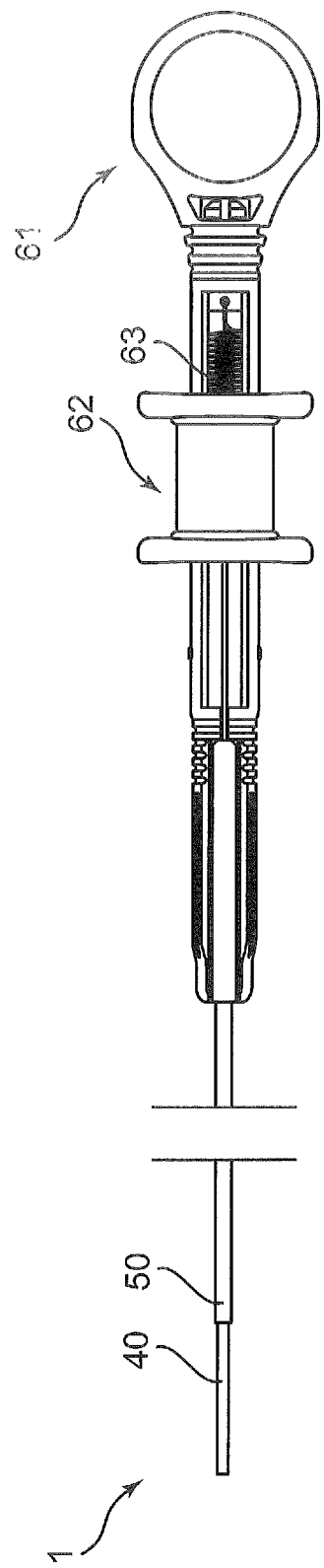

[Fig. 14]
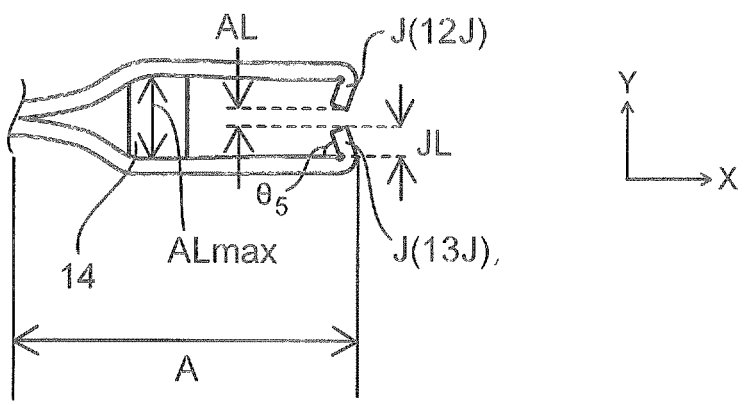
[Fig. 15]
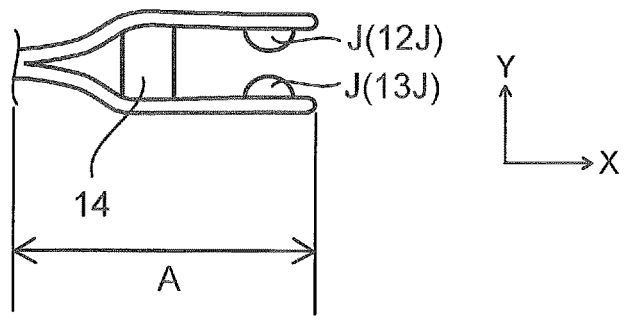
[Fig. 16]
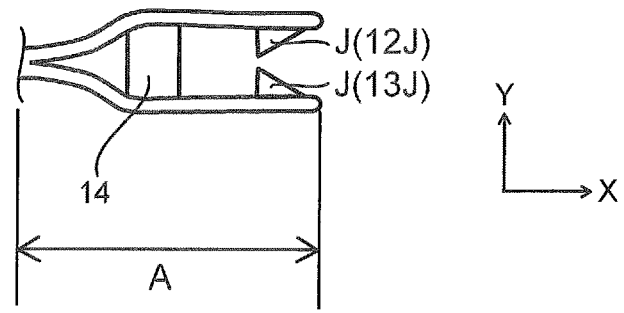

US 10,828,035 B2

CONNECTOR, MEDICAL CLIP DEVICE AND METHOD FOR PRODUCING MEDICAL CLIP DEVICE

TECHNICAL FIELD

The present invention relates to a connector for connecting a medical clip for holding a target site mainly in a treatment with an endoscope with a line member for moving the clip, a medical clip device including the connector, and a method for producing a medical clip device.

BACKGROUND ART

Conventionally, endoscopic submucosal dissection (ESD) and endoscopic mucosal resection (EMR) are adopted for early-stage cancer surgeries with an endoscope on organs such as esophagi or stomachs, which have only a small space for conducting a surgery. In ESD and EMR, excision of a lesion may involve bleeding. Bleeding is treated by a stanching method using high-frequency waves or by directly pinching a blood vessel with a clip. A clip is also used for suturing a site where a lesion has been removed. A clip for these treatments is attached to the end of a line member and is carried to a lesion site through an endoscope.

The clip is connected with the line member by placing a connecting hook on the U-shaped base part of the holding instrument (the clip) in a cartridge (for example, Patent Literatures 1 and 2). Specifically, the connecting hook, which is attached to the end of the line member, is placed in a connecting hole in the clip for connecting the clip with the line member. Generally, for connecting the clip with such a connector, the connector is brought close to a clip in a cartridge or the like. In the clip device disclosed in Patent Literature 1, a clip has a connecting hole, and a connecting hook (a connector) attached to the end of a line member is placed in the connecting hole for connecting the clip with the line member. This connecting operation requires great care when adjusting the direction of the hook attached to the end of the line member with respect to the direction of the base end part of the holding instrument (the clip), for example.

Patent Literature 3 discloses a clip device which facilitates connection of a clip with a line member. In the clip device, a first engaging means provided at the end of a wire (the line member) is engaged with a second engaging means provided at the base end part of the clip for indirectly connecting the clip with the line member. Specifically, a rotational symmetric polygonal-column-shaped stopper for restricting the rotation of the clip body is provided at the end of the first engaging means, and two claws are provided as the second engaging means at the base end part of the clip. Especially FIG. 3 of Patent Literature 3 shows that the first engaging means includes a small-diameter part having a smaller outer diameter than that of the polygonal-column-shaped stopper, at a position proximal to the stopper.

CITATION LIST

Patent Literature

Patent Literature 1
 Japanese Unexamined Patent Application Publication No. 2009-189704
Patent Literature 2
 Japanese Utility Model Registration No. 3159939
Patent Literature 3
 Japanese Unexamined Patent Application Publication No. 2007-275542

SUMMARY OF THE INVENTION

Problems to be Solved by the Invention

A connector including the connecting hook as the engaging part, as described in Patent Literatures 1 and 2, requires a minute adjustment of the angle of the engaging part with respect to the opening in the clip, which makes it difficult to attach the connector to the clip. In addition, even if the line member, which is connected with the clip via the connector, is moved in the distal direction, the clip does not move in the distal direction unless the connecting hook comes into contact with a clip tightening ring. This may make it difficult to move the clip following the movement of the line member especially in the axial direction.

In the clip device of Patent Literature 3, the engaging part including the polygonal-column-shaped stopper at the end of the line member is firmly engaged with the claws at the base end part of the clip, which shortens a response time between the operator's manipulation such as a rotating operation of the line member in his/her hand and the actual movement of the clip at the distal side. If the response time is too short, however, the operator's misoperation may quickly cause an operational error at the clip side. In addition, if the clip or the line member moves in the width direction of the claws at the base end part of the clip, the small-diameter part will be detached from the second engaging means or the two engaging claws, which may release the clip from the line member.

The present invention is based on the above circumstances, and an object of the present invention is to provide a connector that facilitates a connecting operation with a clip, prevents an unintended release of the clip, and suppresses a misoperation of the clip in a holding operation; a medical clip device including the connector; and a method for producing the medical clip device.

Solution to the Problems

A connector of the present invention which is able to achieve the above object, for connecting a medical clip for holding a target site with a line member for moving the clip comprises: a through hole whose depth direction is nonparallel to an axial direction; and a thin part that is formed at least at a part distal to the through hole and is thinner than a distal end of the through hole. The connector of the present invention facilitates the connection of the clip with the line member by engaging the clip in the through hole. The connector of the present invention has a thin part that is formed at least at a part distal to the through hole and is thinner than a distal end of the through hole. The thin part is inserted between two holding members, which face each other, of the clip, which facilitates the engagement of the clip with the connector. After the connector is engaged with the clip, a part of the clip is fastened in the through hole. Even if the clip or the connector moves in any direction, the connection of the clip with the connector holds, unless the clip is deformed by a certain degree of external force. In addition, according to the present invention, only a part of the clip is placed in the through hole, which allows the clip to move in the through hole to a certain degree while being engaged in the through hole. This gives a time lag between the operator's manipulation such as a rotating operation of the line member at the proximal side and the response time when the clip actually moves at the distal side, which suppresses the misoperation of the clip in a holding operation.

It is preferable that the thin part has a section whose thickness becomes thinner toward a distal end of the connector. When the connector is inserted between the two holding members of the clip, the connector easily spreads the two holding members of the clip along that inclination, which facilitates a smooth connection with the clip.

To connect the clip with the connector without resistance, it is preferable that the through hole is formed at a position distal to a center with respect to the axial direction.

From the viewpoint of easily forming the through hole, it is preferable that a cross-sectional shape of the through hole is circular or elliptical.

It is preferable that a depth of the through hole is shorter than a maximum diameter of the connector. This depth of the through hole reduces the force necessary for separating the two holding members of the clip.

In the connector of the present invention, it is preferable that a hollow part that is located proximal to the center with respect to the axial direction, wherein a maximum thickness in a section where the hollow part is formed is thicker than a thickness at the distal end of the through hole. The connector is connected with the line member by inserting the line member into the hollow part. Since the maximum thickness in a section where the hollow part is formed is thicker than the thickness at the distal end of the through hole, the connector easily accommodates the line member.

Since the connector is inserted into the body, it is preferable that the connector is composed of a stainless steel or a Ni—Ti alloy.

A medical clip device comprises: an outer tubular body; an inner tubular body provided in the outer tubular body; a line member placed in the inner tubular body; a clip including a clip body that is disposed at a distal side of the inner tubular body and has two holding members facing each other, and a ring-shaped tightening member that is provided to the clip body; and a connector including a through hole whose depth direction is nonparallel to an axial direction, and a thin part that is formed at least at a part distal to the through hole, is thinner than a distal end of the through hole, and has a connecting part connected to the line member at a proximal side; wherein a holding part for holding a target site is formed at a distal side of the clip body, two engaging parts facing each other are formed at a proximal side of the clip body, and the engaging part is capable of engaging with the through hole. The medical clip device of the present invention has the thin part that is formed at least at a part distal to the through hole, is thinner than a distal end of the through hole. The thin part is inserted between the two holding members to engage the engaging parts of the clip body with the through hole in the connector, which facilitates the connection of the clip with the line member via the connector.

In the medical clip device, it is preferable that the engaging part is formed on an inner surface of the holding member. The engaging parts formed like this enable the engagement of the engaging parts of the clip body in the through hole in the connector while the connector is disposed between the two holding members. This easily aligns the longitudinal direction of the clip body with the axial direction of the connector.

In the medical clip device, the engaging part may be projected in a direction perpendicular to both an opening-and-closing direction and an axial direction of the clip body, and inward in a radial direction. The connector is inserted between the two holding members with these engaging parts while the depth direction of the through hole is perpendicular to the opening-and-closing direction of the clip body, which enables the connection of the connector with the clip while the longitudinal direction of the clip body aligns with the axial direction of the connector.

In the medical clip device, the engaging part may be formed at a proximal end of the holding member. This facilitates the engagement of the clip body with the line member. In addition, the connector can be shorter in the longitudinal direction, which prevents deformation of the connector while in use.

In the medical clip device, it is preferable that a minimum diameter of the through hole is larger than a maximum width of the engaging part. This allows the through hole and the engaging part to be firmly engaged.

In the medical clip device, it is preferable that a distance between the two engaging parts is shorter than a depth of the through hole. The relationship between the distance between the engaging parts and the depth of the through hole prevents the engaging parts from coming out of the through hole.

A method for producing a medical clip device of the present invention comprises steps of: preparing a line member; a clip including a clip body that has two holding members facing each other and that has an engaging part formed at a proximal side and a holding part formed at a distal side for holding a target site, and a ring-shaped tightening member attached to the clip body; and a connector including a through hole whose depth direction is nonparallel to an axial direction, and a thin part that is formed at least at a part distal to the through hole and is thinner than a distal end of the through hole; and engaging the engaging part with the through hole. The method for producing the medical clip device of the present invention facilitates the connection of the clip with the line member by the step of engaging the engaging part of the clip body with the through hole in the connector.

It is preferable that the method for producing the medical clip device of the present invention further comprises the step of connecting the connector to a distal side of the line member. The connector is connected to the line member by this step, which facilitates the connection of the clip with the line member via the connector.

Effects of the Invention

The connector of the present invention facilitates the connection of the clip with the line member. The thin part that is thinner than a distal end of the through hole of the connector is inserted between two holding members, which facilitates the engagement of the clip with the connector. After the connector is engaged with the clip, a part of the clip is fastened in the through hole. Even if the clip or the connector moves in any direction, the connection of the clip with the connector holds, unless the clip is deformed by a certain degree of external force. In addition, according to the present invention, only a part of the clip is placed in the through hole, which allows the clip to move in the through hole to a certain degree while being engaged in the through hole. This gives a time lag between the operator's manipulation such as a rotating operation of the line member at the proximal side and the response time when the clip actually moves at the distal side, which suppresses the misoperation of the clip in a holding operation.

In a medical clip device of the present invention, the thin part that is thinner than a distal end of the through hole of the connector is inserted between the two holding members to engage the engaging parts of the clip body with the through hole in the connector, which facilitates the connection of the clip with the line member via the connector.

A method for producing a medical clip device of the present invention facilitates the connection of the clip with the line member by the step of engaging the engaging part of the clip body with the through hole in the connector.

BRIEF DESCRIPTION OF THE DRAWINGS

FIG. 1 is a side view of a connector in a state engaged with a clip according to the present invention.

FIG. 2 is a perspective view of a connector in a state engaged with a clip according to the present invention.

FIG. 3 is a cross-sectional view taken along a line III-III shown in FIG. 2.

FIG. 4 is a perspective view of a connector of the present invention.

FIG. 5 is a plan view of a connector of the present invention.

FIG. 6 is a side view of a connector of the present invention.

FIG. 7 is a side view of a modified embodiment of a connector of the present invention.

FIG. 8 is a side view of a modified embodiment of a connector of the present invention.

FIG. 9 is a side view of a modified embodiment of a connector of the present invention.

FIG. 10 is a side view of a modified embodiment of a connector of the present invention.

FIG. 11 is a perspective view of a modified embodiment of a connector of the present invention.

FIG. 12 is a plan view of a medical clip device of the present invention.

FIG. 13 is a plan view of a medical clip device of the present invention.

FIG. 14 is a side view of a medical clip according to the present invention.

FIG. 15 is a side view of a medical clip according to the present invention.

FIG. 16 is a side view of a medical clip according to the present invention.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

1. Connector

In the present invention, a medical clip is an instrument for holding a target site (a lesion in an organ) in an endoscopic operation for sealing, countertraction, stanching, suturing, or marking. In this specification, a medical clip may simply be called "a clip." In "1. Connector", description will be made by illustrating an example clip, which includes a clip body having holding parts with two holding members facing each other for holding a target site at the distal side, and two engaging parts facing each other at the proximal side; and a ring-shaped tightening member attached to the clip body; however, the clip is not limited to this aspect.

In the present invention, a line member is connected with the connector that moves by traction the clip via the connector.

In the present invention, an axial direction refers to a direction from a through hole of the connector to an operator's hand side, and a proximal side in the axial direction refers to a direction of an operator's hand side, while a distal side refers to a direction opposite to the proximal side. Also, in the present invention, a radial direction refers to a radial direction of a tightening member, and an inner side in the radial direction refers to a direction toward a center of the tightening member, while an outer side refers to a radiation direction of the tightening member. In addition, a width of a holding member of the clip body refers to a length of the holding member in a direction perpendicular to a longitudinal direction of the clip body in a plan view of the clip body.

FIG. 1 is a side view of a connector in a state engaged with a clip according to the present invention. As shown in FIG. 1, the connector 20 of the present invention is used to connect a medical clip 10 for holding a target site with a line member 30 for moving the clip 10. The connector 20 of the present invention includes a through hole 21 whose depth direction is nonparallel to an axial direction and a thin part that is formed at least at a part distal to the through hole 21 and is thinner than a distal end of the through hole 21.

The connector 20 is connected with the clip 10 in the following way, for example. First, the connector 20 with the line member 30 is prepared. Then, the connector 20 is positioned with respect to the clip 10. The connector 20 is moved toward the clip body 11 in the distal direction and then the distal end part of the connector 20 is pushed into the proximal end part of the clip body 11 so that a thin part of the connector 20, which is thinner than the distal end of the through hole 21, is disposed between the two holding members 12 and 13. As a result, engaging parts J (12J, 13J) of the clip body 11 are engaged with the through hole 21 in the connector 20, which connects the clip body 11 with the connector 20. In this way, the connector 20 of the present invention facilitates the connection of the clip 10 with the line member 30.

The engaging parts J of the clip body 11 may be released from the through hole 21 if the distance between the paired engaging parts J, J exceeds the thickness of the section having the through hole 21 due to a deformation of the clip 10, for example, and the engaging parts J come out of the through hole 21. As described above, however, after the connector 20 is engaged with the clip 10, the engaging parts J of the clip body 11 are fastened in the through hole 21 and the connection of the clip 10 with the connector 20 hardly breaks unless the clip 10 is deformed by a certain degree of external force. Since the connection holds all around the through hole 21, the connection is secure and not broken unintentionally. In addition, even if the engaging parts J move in the depth direction of the through hole 21, the inner surfaces of the holding members 12 and 13 come into contact with the surface of the connector 20, which restricts the movement of the engaging parts J.

The axial movement or the X-axis movement of the line member 30 will now be described. When the line member 30 is moved in the distal direction, the proximal sides of the engaging parts J come into contact with the proximal-side inner wall of the through hole 21 and then the clip 10 is moved in the distal direction following the movement of the line member 30. When the line member 30 is moved in the proximal direction, the distal sides of the engaging parts J come into contact with the distal-side inner wall of the through hole 21 and then the clip 10 is moved in the proximal direction following the movement of the line member 30.

Next, a rotating operation of the line member 30 will be described with reference to FIGS. 2 and 3. FIG. 2 is a perspective view of a connector in a state engaged with a clip according to the present invention, and FIG. 3 is a cross-sectional view taken along a line III-III shown in FIG. 2. As shown in FIGS. 2 and 3, when the line member 30 is rotated (around the axial direction of the line member 30 or the X-axis direction in FIGS. 2 and 3), parts of the side surfaces of the engaging parts J come into contact with the inner wall of the through hole 21 and then the clip 10 is rotated following the rotation of the line member 30. It is especially preferable that the side surfaces of the engaging parts J not facing the axial direction come into contact with the inner wall of the through hole 21.

In the present invention, since only a part of the clip body 11, for example, only the engaging parts J are engaged in the through hole 21, the clip 10 is engaged in the through hole 21 while being able to move in the through hole 21 to a certain degree. This gives a time lag between the operator's manipulation such as a rotating operation of the line member 30 at the proximal side and the response time when the clip 10 actually moves at the distal side, which suppresses the misoperation of the clip 10 in a holding operation.

A specific structure of the connector 20 will be described with reference to FIGS. 1, 4 to 6. FIGS. 4 to 6 are a perspective view, a plan view and a side view of a connector of the present invention, respectively.

The connector 20 has the axial direction (the X-axis direction in FIGS. 4 to 6) and the radial direction, and is in the form of a column such as a cylindrical column or a rectangular column. The size of the connector 20 may appropriately be determined in view of the size of the clip 10 to be connected with, the outer diameter of the line member 30, and the inner diameter of an inner tubular body (described below) for accommodating the connector 20 in a closing operation of the clip 10. Specifically, the outer diameter of the connector 20 may be 0.3 mm or more and 4 mm or less, and the total axial length 20L of the connector 20 may be 3 mm or more and 10 mm or less, for example.

To appropriately ensure both an open area of the through hole 21 in the connector 20 and a hollow part 26 (described in detail below) for accepting the line member 30, the total axial length 20L of the connector 20 should preferably be equal to or more than double the maximum diameter 20R of the connector 20, more preferably equal to or more than triple the maximum diameter 20R of the connector 20, or much more preferably equal to or more than three and half times the maximum diameter 20R of the connector 20.

The connector 20 includes a through hole 21 whose depth direction is nonparallel to an axial direction (the X-axis direction). It is preferable that the depth direction of the through hole 21 is inclined by 45 degrees or more and 135 or less with respect to the axial direction of the connector 20. It is more preferable that the depth direction of through hole 21 is perpendicular to the axial direction of the connector 20. It is preferable that the depth direction of through hole 21 is perpendicular to the longitudinal direction of the clip body 11. This aligns the axial direction of the connector 20 with longitudinal direction of the clip body 11, which matches the operator's operational movement with the actual movement of the clip 10. In FIGS. 1 and 6, the depth direction of the through hole 21 is in the Y-axis direction, however, the depth direction of the through hole 21 may be in the Z-axis direction.

It is preferable that a depth of the through hole 21 is shorter than the maximum diameter 20R of the connector 20. This depth of the through hole 21 reduces the force necessary for separating the two holding members 12 and 13 of the clip 10. Here, the depth of the through hole 21 refers to a minimum depth of the through hole 21. The depth of the through hole 21 should preferably be equal to or less than half the maximum diameter 20R of the connector 20, or more preferably equal to or less than quarter the maximum diameter 20R of the connector 20.

The inner diameter of the through hole 21 may be constant or vary in the depth direction of the through hole 21. FIG. 7 is a side view of a modified embodiment of the connector of FIG. 6. As shown in FIG. 7, the through hole 21 has an inner diameter 21RC at the radial center YC of the connector 20 and an inner diameter 21RE at an open end of the through hole 21. The inner diameter 21RC should preferably be larger than the inner diameter 21RE. This is preferable especially because the engaging claws of the clip 10 can easily be caught in the through hole 21 in the connector 20 when the engaging claws are engaged in the through hole 21.

The axial position of the through hole 21 is not limited, however, as shown in FIGS. 5 and 6, the through hole 21 should preferably be formed at a position distal to the axial center XC to facilitate a smooth connection of the clip 10 with the connector 20.

A cross-sectional shape of the through hole 21 is not limited, for example, may be circular, elliptical, polygonal, or a combination thereof. Among them, from the viewpoint of easily forming the through hole 21, it is preferable that the cross-sectional shape of the through hole 21 is circular or elliptical. FIG. 5 shows an example that the cross-sectional shape of the through hole 21 is circular.

To facilitate the engagement of the engaging parts J of the clip body 11 with the through hole 21 in the connector 20 as well as to ensure the strength of the connector 20, the maximum diameter 21R of the through hole 21 should preferably be 40% or more of the maximum diameter 20R of the connector 20, more preferably 50% or more of the maximum diameter 20R of the connector 20, and much more preferably 60% or more of the maximum diameter 20R of the connector 20, however, preferably be 95% or less of the maximum diameter 20R of the connector 20, more preferably 90% or less of the maximum diameter 20R of the connector 20, and much more preferably 85% or less of the maximum diameter 20R of the connector 20.

To appropriately ensure both an open area of the through hole 21 and lengths of the line member 30 and the hollow part 26, the ratio of the maximum diameter 21R of the through hole 21 in the total axial length 20L of the connector 20 in the axial direction (the X-axis direction) should preferably be 10% or more, more preferably 15% or more, further preferably 20% or more, and preferably be 50% or less, more preferably 45% or less, further preferably 40% or less.

The section where an opening of the through hole 21 is formed in the axial direction in FIGS. 5 and 6 is defined as an opening section 23. The opening section 23 may have a first major surface 23A and a second major surface 23B that face each other. In FIG. 6, the through hole 21 is open in both the first major surface 23A and the second major surface 23B. In this case, the maximum thickness of the opening section 23 corresponds to the maximum distance between the first major surface 23A and the second major surface 23B.

The thickness of the opening section 23 may be constant or greater at a part than the other area. The opening section 23 may become thicker toward the proximal side or toward the distal side. The opening section 23 may taper from the proximal end to the distal end.

The first major surface 23A and the second major surface 23B are formed by drilling a part of the connector 20 with a drill or by wire processing, for example.

In FIG. 6, the first major surface 23A is parallel to the second major surface 23B, however, at least one of the first major surface 23A and the second major surface 23B may be inclined with respect to the axial direction of the connector 20. The angle between the plane direction of the first major surface 23A and the axial direction of the connector 20 is defined as a first inclination angle $\theta_1$, and the angle between the plane direction of the second major surface 23B and the axial direction of the connector 20 is defined as a second inclination angle $\theta_2$. Each of the first inclination angle $\theta_1$ and the second inclination angle $\theta_2$ should preferably be 10° or less, more preferably 5° or less, and much more preferably 3° or less. In case of the opening section 23 that is slightly inclined at a positive angle with respect to the axial direction, the paired engaging parts J of the clip body 11 gradually spread along the inclination of the opening section 23, which facilitates the insertion of the engaging parts J into the through hole 21. After the clip 10 is connected with the connector 20, the connection hardly breaks unless the proximal side of the clip 10 spreads and the distance between the paired engaging parts J, J exceeds the thickness of the opening section 23. The engaging parts J thus hardly come out of the through hole 21.

Alternatively, each of the first inclination angle $\theta_1$ and the second inclination angle $\theta_2$ should preferably be −10° or more, more preferably −5° or more, or much more preferably −3° or more. In case of the opening section 23 that is slightly inclined at a negative angle with respect to the axial direction, during the connecting operation of the clip 10 with the connector 20, the paired engaging parts J, J go over the thickest part of the opening section 23 and then come close to each other again due to the elastic recovery of the clip body 11, which completes the engagement of the engaging parts J in the through hole 21. In addition, the opening section 23, which gradually becomes thicker toward the distal side, suppresses the engaging parts of the clip body 11 from coming out of the through hole 21 unintentionally and breaking the connection when the engaging parts J move away from the through hole 21 in the distal direction after the connection of the clip 10 with the connector 20. When the clip 10 is disconnected from the connector 20 intentionally, the engaging parts J of the clip body 11 gradually spread along the inclination of the opening section 23, which facilitates the disconnecting operation. If the first inclination angle $\theta_1$ or the second inclination angle $\theta_2$ is too large (in both positive and negative cases), the angle between the longitudinal direction of the clip body 11 and the axial direction of the connector 20 becomes too large the clip body 11 is connected with the connector 20. This is thus not preferable.

FIG. 8 is a side view of a modified embodiment of the connector of FIG. 6. In FIG. 8, the plane direction of the first major surface 23A is parallel to the axial direction of the connector 20 and the first inclination angle $\theta_1$ is thus 0° while the second inclination angle $\theta_2$ is approximately 3°. As described above, the first inclination angle $\theta_1$ may be equal to or larger than the second inclination angle $\theta_2$.

As shown in FIG. 1 and FIGS. 4 to 6, each of the first major surface 23A and the second major surface 23B should preferably be flat. This reduces the friction between the connector 20 and the clip 10 when the clip 10 is connected with the connector 20.

As shown in FIGS. 1, 2 and 6, the connector 20 includes a thin part that is formed at least at a part distal to the through hole 21 and is thinner than a distal end of the through hole 21. The thin part easily enters the space between the two holding members 12 and 13 of the clip 10, which facilitates the engagement of the connector 20 with the clip 10.

It is preferable that the thin part has a section whose thickness becomes thinner toward a distal side. When the connector 20 is inserted between the two holding members 12 and 13 of the clip, the connector easily spreads the two holding members 12 and 13 of the clip along that inclination, which facilitates a smooth connection with the clip.

The distal side of the connector 20 is the section that first comes into contact with the clip 10 when the clip 10 is connected with the connector 20. The distal end part including the distal end of the thin part is defined as a guide part, which facilitates the engagement of the connector 20 with the clip 10.

As shown in FIG. 6, the guide part 22 should preferably become thinner toward the distal end. The guide part 22 should preferably have no steps. When the connector 20 is inserted between the two holding members 12 and 13 of the clip, the two holding members 12 and 13 easily spread along the inclination of the guide part 22, which facilitates a smooth connection with the clip. For this purpose, as shown in FIG. 9, the guide part 22 may taper toward the distal end.

As shown in FIG. 6, the inclination angle in the guide part 22 of the connector 20 (a third inclination angle $\theta_3$) should preferably be less than 180°, more preferably 150° or less, further preferably 110° or less, further more preferably 90° or less, particularly 70° or less. From the viewpoint of ensuring the strength of the guide part 22, the third inclination angle $\theta_3$ should preferably be 10° or more, more preferably 20° or more, further preferably 30° or more.

To facilitate the insertion of the connector 20 between the two holding members 12 and 13 of the clip body 11, the line bisecting the third inclination angle $\theta_3$ should preferably be in the axial direction of the connector 20, as shown in FIGS. 6 and 8.

FIG. 9 is a side view of a modified embodiment of the connector of FIG. 6. As shown in FIG. 9, it is preferable that there are no steps between the guide part 22 and the opening section 23. This facilitates a smooth movement of the clip 10 from the guide part 22 to the opening section 23.

As shown in FIG. 9, it is preferable that the guide part 22 is adjacent to the opening section 23 and the thicknesses of the guide part 22 and the opening section 23 continuously vary from the guide part 22 to the opening section 23. This facilitates a further smooth movement of the clip 10 from the guide part 22 to the opening section 23.

A maximum thickness in the opening section 23 should preferably be equal to or less than 1.5 times the thickness of a proximal end of the guide part 22, more preferably equal to or less than 1.3 times the thickness of a proximal end of the guide part 22, further preferably equal to or less than 1.1 times the thickness of a proximal end of the guide part 22. This thickness in the opening section 23 reduces the force necessary for separating the two holding members 12 and 13 of the clip 10.

FIG. 10 is a side view of a modified embodiment of the connector of FIG. 6. As shown in FIG. 10, the extending direction of the line bisecting the third inclination angle $\theta_3$ may not be in the axial direction of the connector 20. The connector 20 like this enables simple formation of the guide part 22 while being able to spread the two holding members 12 and 13 of the clip body 11.

To facilitate the engagement of the clip 10 with the connector 20 as well as to suppress the breakage of the engagement, the distance (denoted by the reference AL in FIG. 14 described below) between the two engaging parts 12J and 13J of the clip body 11 should preferably be greater than the thickness of at least a part of the guide part 22 and smaller than the maximum thickness of the opening section 23. The distance AL between the base end parts A of the two holding members 12 and 13 facing each other means the distance under the condition that the connector 20 is not engaged with the clip 10.

To prevent the clip 10 from being polluted before use, the clip 10 is generally sealed in a cartridge (not shown). To connect the connector 20 with the clip 10, which is held in a fixed direction in the cartridge, the connector 20 should preferably be inserted in the cartridge so that the projecting direction of the engaging parts J of the clip 10 is substantially parallel to the depth direction of the through hole 21. When the connector 20 is small, however, inserting the connector 20 in an appropriate direction is not easy. To facilitate the insertion of the connector 20 into the cartridge in an appropriate direction, the connector 20 may have a direction adjusting part 27. The direction adjusting part 27 may be an inclined surface of the connector 20 (shown in FIGS. 4 and 6), or a raised or recessed area to engage with the shape of the cartridge (not shown).

As shown in FIG. 6, when the direction adjusting part 27 is an inclined surface, the inclination angle of the inclined surface is defined as a fourth inclination angle $\theta_4$. The fourth inclination angle $\theta_4$ should preferably be 45° or less, more preferably 40° or less, and much more preferably 35° or less, however, preferably be 5° or more, more preferably 10° or more, and much more preferably 15° or more. When the connector 20 is inserted into the cartridge, the inclined surface as the direction adjusting part 27 comes into contact with the inner wall of the cartridge. The fourth inclination angle $\theta_4$ in the above range facilitates the axial rotation of the connector 20 in the engaging direction of the engaging parts J of the clip body 11 in the through hole 21.

With reference to FIG. 11, another structure of the through hole 21, which is different from those shown in FIGS. 1 to 10, will now be described. FIG. 11 is a perspective view of a modified embodiment of the connector of the present invention. As shown in FIG. 11, the connector 20 should preferably have a lower part of the inner wall of the through hole 21 than the other part of the inner wall. It is especially preferable that the connector 20 has the lower part of the inner wall of the through hole 21 at the distal side and has the higher part of the inner wall at the proximal side. This enables the engaging parts J of the clip body 11 to easily be engaged in the through hole 21 through the lower part of the inner wall of the through hole 21. In addition, when the connector 20 is axially rotated, the clip 10 easily comes into contact with the higher part of the inner wall of the through hole 21 in the connector 20 and the engaging parts J hardly come out of the through hole 21, which is preferable.

To suppress the engaging parts J from easily coming out of the through hole 21, the height of the higher part of the inner wall of the through hole 21 should preferably be equal to or more than double the height of the lower part of the inner wall of the through hole 21, more preferably equal to or more than triple the height of the lower part of the inner wall of the through hole 21, and much more preferably equal to or more than four times the height of the lower part of the inner wall of the through hole 21. To suppress the outer diameter of the connector 20 from being too large, the height of the higher part of the inner wall of the through hole 21 should preferably be equal to or less than ten times the height of the lower part of the inner wall of the through hole 21, more preferably equal to or less than eight times the height of the lower part of the inner wall of the through hole 21, and much more preferably equal to or less than six times the height of the lower part of the inner wall of the through hole 21.

As shown in FIGS. 1, 4 to 6, it is preferable that a hollow part 26 that is located proximal to the center XC with respect to the axial direction in the connector 20. The connector 20 is connected with the line member 30 by inserting the line member 30 into the hollow part 26.

A method for connecting the hollow part 26 to the line member 30 is not limited, for example, mechanical securing such as fitting, using screws, or caulking, welding such as using laser or brazing, bonding using adhesives such as polyurethane adhesives, epoxy adhesives, cyano adhesives, or silicone adhesives can be used.

The connector 20 and the line member 30 may be integrally formed. The connector 20 can be connected with the clip 10 by providing the through hole 21 of the present invention at the distal end part of the line member 30.

As shown in FIGS. 1, 4 to 6, the hollow part 26 should preferably be formed along the axial direction of the connector 20. The hollow part 26 formed along the axial direction of the connector 20 can align the axial direction of the line member 30 with the axial direction of the connector 20. To insert the line member 30 into the hollow part 26, the inner diameter of the hollow part 26 is larger than the outer diameter of the line member 30.

It is preferable that a maximum thickness in a section where the hollow part 26 is formed is thicker than a thickness at the distal end of the through hole 21. Since the maximum thickness in the section where the hollow part 26 is formed is thicker than the thickness at the distal end of the through hole 21, the connector 20 easily accommodates the line member 30.

Specifically, the maximum thickness in the section where the hollow part 26 is formed should more preferably be equal to or more than 2.5 times the maximum thickness of the opening section 23, further preferably equal to or more than three times the maximum thickness of the opening section 23. The maximum thickness in the section where the hollow part 26 is formed should preferably be 80% to 95% of an inner diameter of the inner tubular body 40. This suppresses the connector 20 from being axially displaced in the inner tubular body 40, which enables a smooth rotation of the connector 20.

To surely connect the connector 20 with the line member 30, the total length 20L of the connector 20 should preferably be equal to or more than three times the length 26L of the hollow part 26 in the axial direction, more preferably equal to or more than 3.5 times the length 26L of the hollow part 26 in the axial direction, further preferably equal to or more than four times the length 26L of the hollow part 26 in the axial direction, preferably equal to or less than 15 times the length 26L of the hollow part 26 in the axial direction, more preferably equal to or less than 13 times or less of the length 26L of the hollow part 26 in the axial direction, further preferably equal to or less than 10 times the length 26L of the hollow part 26 in the axial direction.

As shown in FIG. 4, the proximal end part of the connector 20 should preferably have a conical shape having a smaller outer diameter toward the proximal side. The proximal end part of the connector 20 having a smaller outer diameter toward the proximal side suppresses the line member 30 from being broken due to a large difference between the outer diameter of the hollow part 26 and the outer diameter of the line member 30.

Since the connector 20 is inserted into the body, it is preferable that the connector 20 is composed of a stainless steel or a Ni—Ti alloy. The connector 20 should preferably be composed of a metal material such as a Ni—Ti alloy or a stainless steel such as SUS303, SUS304, SUS631, or a synthetic resin material such as polyolefin resin such as PP, PE.

2. Medical Clip Device

FIGS. 12 and 13 are plan views of a medical clip device of the present invention. A medical clip device 1 of the present invention includes an outer tubular body 50, an inner tubular body 40, a line member 30, a clip 10 and a connector 20. FIG. 12 illustrates the clip 10, the connector 20, and a part of the line member 30 projecting from the inner tubular body 40, and FIG. 13 illustrates the clip 10, the connector 20, and the line member 30 accommodated in the inner tubular body 40. The connector 20 constituting the clip device 1 is the one as described in "1. Connector."

(1) Outer Tubular Body

The outer tubular body 50 protects a forceps opening of an endoscope, the inner wall of a forceps channel and body tissues other than a target tissue from being damaged by the clip 10 while the clip 10 is being sent from the forceps opening of an endoscope through the forceps channel to near the target tissue.

The outer tubular body 50 preferably has balanced combination of flexibility to bend along the shape of a body cavity and rigidity to reach a target tissue. The outer tubular body 50 may be made of a coiled metal member, a plurality of short cylindrical joint pieces rotatably connected in the axial direction, or a synthetic resin, and should preferably be made of the synthetic resin. The outer tubular body 50 should preferably be made of transparent or translucent materials so that the operator can see the position of the inner tubular body 40 in the outer tubular body 50.

(2) Inner Tubular Body

The line member 30 is placed at an inner lumen of the inner tubular body 40, and the clip 10 is disposed at a distal side of the inner tubular body 40. The inner tubular body 40 allows to adjust an opening/a closing of the clip 10 by being moved with respect to the clip 10 back and forth in the axial direction. The inner tubular body 40 preferably has balanced combination of flexibility to bend along the shape of a body cavity and rigidity to reach a target tissue.

The inner tubular body 40 may be made of a coiled metal member, a plurality of short cylindrical joint pieces rotatably connected in the axial direction, or a synthetic resin.

The outer tubular body 50 and the inner tubular body 40 may be composed of polyamide resin such as nylon, polyolefin resin such as polypropylene (PP), polyethylene (PE), polyester resin such as polyethylene terephthalate (PET), poly aromatic polyether ketone resin such as polyether ether ketone (PEEK), polyimide resin, fluorine resin such as polytetrafluoroethylene (PTFE), tetrafluoroethylene-perfluoroalkylvinylether copolymer (PFA), ethylene-tetrafluoroethylene copolymer (ETFE). In view of slipperiness, the synthetic resins for the outer tubular body 50 should preferably be different from the synthetic resins for the inner tubular body 40.

(3) Line Member

The line member 30 is a member for traction of the clip 10 for holding a target site via the connector 20. The line member 30 is placed in the inner tubular body 40.

The line member 30 should preferably be composed of a material having biocompatibility and strength, may be composed of metal wire rod such as a stainless steel wire and a carbon steel wire, or plastic fibers such as polyamide resin such as nylon, polyolefin resin such as PP, PE, polyester resin such as PET, poly aromatic polyether ketone resin such as PEEK, polyimide resin, fluorine resin such as PTFE and PFA.

The metal wire rod may be a single wire or a stranded wire consisting of multiple wires. A metal wire rod of a single wire transmits torque to the clip 10 well. A metal wire rod of a stranded wire easily recovers the original shape even if it is deformed, which is preferable.

In view of an application of the clip device 1, the line member 30 may be composed of a rigid wire rod or a flexible wire rod.

To smoothly move the line member 30, a length of the line member 30 should preferably be equal to or more than 1.1 times that of the inner tubular body 40, more preferably equal to or more than 1.3 times that of the inner tubular body 40, further preferably equal to or more than 1.5 times that of the inner tubular body 40.

The maximum length of the line member 30 is not particularly limited, to prevent operating of the line member 30, the length of the line member 30 should preferably be equal to or less than 3.4 times that of the inner tubular body 40, more preferably equal to or less than 3.2 times that of the inner tubular body 40, further preferably equal to or less than 3.0 times that of the inner tubular body 40.

(4) Clip

As shown in FIG. 1, the clip 10 includes a clip body 11 and a tightening member 15. The clip body 11 is a member for holding a target site such as a lesion, is disposed at a distal side of the inner tubular body 40 and has two holding members 12 and 13 facing each other. The present invention can be applied to a clip without a tightening member.

The clip 10 is closed in the following way. First, the tightening member 15 is placed around the proximal-side outer part of the clip body 11 in an open state. Then, the tightening member 15 is moved to the distal side of the clip body 11. As the tightening member 15 moves toward the distal side, the tightening member 15 applies an inward pressure to the holding members 12 and 13 in the radial direction, so that the holding members 12 and 13 come close to each other until the clip 10 closes.

In the clip body 11, one holding member 12 and the other holding member 13 are located so as to face each other. The clip body 11 has holding parts D for holding a target site at the distal side and two engaging parts J facing each other at the proximal side. The medical clip device 1 of the present invention facilitates the connection of the clip 10 with the line member 30 vis the connector 20 by engaging the engaging parts J of the clip body 11 with the through hole 21 in the connector 20. To easily hold the target site, as shown in FIG. 1, in the clip body 11, the holding parts D are preferably formed at the distal sides of one holding member 12 and the other holding member 13, respectively.

As shown in FIG. 1, the holding members 12 and 13 of the clip body 11 may be had a curved part B proximal to the holding part D and a base end part A, respectively. The holding parts D directly hold a target site and are disposed at the distal side of the holding members 12 and 13. The curved parts B are curved inward in the radial direction of the tightening member 15, The base end parts A are disposed at positions proximal to the curved parts B. The curved parts B of the holding members 12 and 13 easily bend, so that the distal side of the clip body 11 spreads outward in the radial direction to be properly positioned with respect to a target site for holding.

As shown in FIG. 1, to keep a constant distance between the holding members 12 and 13 at the proximal sides of the base end parts A to facilitate the engagement of the clip body 11 with the connector 20, a reinforcing member 14 may be provided for connecting a base end part 12A of the holding member 12 with a base end part 13A of the holding member 13. Not to impede the engagement of the clip body 11 with the connector 20, the reinforcing member 14 should preferably be provided at the distal sides of the base end parts A. The reinforcing member 14 should preferably be composed of materials similar to the materials for the holding members 12 and 13, and the thickness of the reinforcing member 14 may be determined as the thickness of the holding members 12 and 13 is. The reinforcing member 14 may be mounted by mechanical fastening such as screwing and caulking, welding, or bonding, as the connector 20 is connected with the line member 30. The reinforcing member 14 may be omitted, and the clip body 11 may be formed by cutting a notch in one metal plate and bending the plate to form the two holding members 12 and 13 integrally.

In the clip device 1 of the present invention, the connector 20 is inserted between the two holding members 12 and 13 in the distal direction to engage the engaging parts J (12J, 13J) of the clip body 11 in the through hole 21 in the connector 20. It is thus preferable that the two holding members 12 and 13 are not connected with each other at the proximal end of the clip body 11. It is also preferable that the engaging parts J are provided at the proximal sides of the base end parts A of the clip body 11, and it is more preferable that the engaging parts J are provided at the proximal ends of the holding members 12 and 13.

To ensure the engagement of the engaging parts J in the through hole 21, the two engaging parts J of the clip body 11 should preferably project inward in the radial direction. As shown in FIG. 1, the engaging parts J may project inward in the radial direction and in the opening-and-closing direction of the clip body 11. The engaging parts J formed like this enable the engagement of the engaging parts J of the clip body 11 in the through hole 21 in the connector 20 while the connector 20 is disposed between the two holding members 12 and 13. This easily aligns the longitudinal direction of the clip body 11 with the axial direction of the connector 20.

The engaging parts J may be projected in a direction perpendicular to both an opening-and-closing direction and an axial direction of the clip body 11, and inward in a radial direction (not shown). The connector 20 is inserted between the two holding members 12 and 13 with these engaging parts J while the depth direction of the through hole 21 is perpendicular to the opening-and-closing direction of the clip body 11, which enables the connection of the connector 20 with the clip 10 while the longitudinal direction of the clip body 11 aligns with the axial direction of the connector 20.

In the clip device 1, it is preferable that the engaging parts J of the clip body 11 are formed on an inner surface of the holding members 12 and 13. The engaging parts J formed like this enable the engagement of the engaging parts J of the clip body 11 in the through hole 21 in the connector 20 while the connector 20 is disposed between the two holding members 12 and 13. This easily aligns the longitudinal direction of the clip body 11 with the axial direction of the connector 20.

The size and the shape of the engaging parts J of the clip body 11 is not particularly limited as long as the engaging parts J engage with the through hole 21 in the connector 20. Concrete structure examples of the engaging parts J will be described with reference to FIGS. 14 to 16. FIGS. 14 to 16 are side views of a clip body according to the present invention. FIG. 14 shows that the engaging parts J of the clip body 11 are engaging claws, FIGS. 15 and 16 show that the engaging parts J of the clip body 11 are projections.

As shown in FIG. 14, the engaging parts J may be engaging claws formed at the proximal side of the clip body 11. The engaging parts J are formed at the proximal end of the clip body 11 by bending the proximal side of the clip body 11, for example. The engaging parts J thus easily come close to the through hole 21, which facilitates their engagement. The size and angle of the engaging claws may appropriately be determined in view of the shape and depth (height) of the through hole 21 in the connector 20. The length JL of the engaging claws should preferably be equal to or less than half the maximal distance ALmax between the base end parts A of the two holding members 12 and 13 facing each other, and may be one quarter or more and three quarters or less of the maximal distance ALmax. The angle $\theta_5$ between the engaging claws and the respective base end parts A of the holding members 12 and 13 should preferably be an acute angle. The two engaging claws may be in contact with each other (not shown). The maximal distance ALmax between the base end parts A of the two holding members 12 and 13 facing each other means the maximum distance under the condition that the connector 20 is not engaged with the clip 10.

As shown in FIGS. 15 and 16, the engaging parts J may be projections at the proximal side of the clip body 11. Specifically, the projections should preferably project inward in the radial direction of the holding members 12 and 13 of the clip body 11. This facilitates the insertion of the projections into the through hole 21 when the connector 20 is inserted between the two holding members 12 and 13 from the proximal side of the clip body 11. The shape of the projections may be a dome shape, an elliptical dome shape, a cylindrical shape, a prism shape, a conical shape, or a pyramidal shape, for example.

FIG. 15 illustrates dome-shaped projections. As shown in FIG. 15, the dome-shaped projections reduce the friction between the holding members 12 and 13 of the clip body 11 and the projections, which facilitates the engagement of the projections in the through hole 21. Elliptical-dome-shaped projections have a similar advantageous effect.

As shown in FIG. 16, the projections may be wedge-shaped claws. Specifically, the distance AL between the projections on the two holding members 12 and 13 should preferably become smaller toward the distal sides. A large distance AL at the proximal sides facilitates the insertion of the connector 20 between the holding members 12 and 13 while a small distance AL at the distal sides facilitates the engagement of the engaging parts J in the through hole 21.

It is preferable that a minimum diameter of the through hole 21 is larger than a maximum width of the engaging part J. By setting the size of the through hole 21 and the engaging part J in this manner, the through hole 21 and the engaging part J can be firmly engaged. The maximum width of the engaging parts J is the length of the engaging parts in the direction perpendicular to the longitudinal direction of the clip body when the clip body is viewed in a plane view.

It is preferable that the distance AL between the two engaging parts 12J and 13J is shorter than a depth of the through hole 21. The relationship between the distance between the depth (height) of the through hole 21 and the engaging parts J prevents the engaging parts J from coming out of the through hole 21.

The holding parts D directly hold a target site and are disposed at the distal sides of the holding members 12 and 13.

To enhance the rigidity of the holding parts D of the holding members 12 and 13, at least a part of the cross section perpendicular to the longitudinal direction of the holding parts D should preferably have an arc shape projecting outward in the radial direction. For example, at least a part of the holding parts D should preferably be in the form of a semi cylinder. The curvature radius of the holding parts D, which have an arc-shaped cross section perpendicular to the longitudinal direction, may be determined in view of the shape of the inner space of the inner tubular body 40 or the shape of the forceps channel.

The holding parts D should preferably have a claw part G at the distal sides. When the holding parts D hold a target site, the claw parts G cut into the target site to firmly hold the target site. To enable the claw parts G to easily cut into a target site and enhance the stability in a holding operation, the claw parts G may be in the form of teeth. The claw parts G having teeth shape may engage with each other so that the claw part 11G of the holding member 12 engages with the claw part G of the holding member 13 of the clip 10 in a closed state. The shape of each tooth may be a polygonal shape such as a triangular shape, a rectangular shape, or a trapezoidal shape.

As shown in FIG. 1, the two holding members 12 and 13 should preferably be in contact with each other at the proximal end parts of the curved parts B. This enables the adjustment of the degree of opening of the clip body 11 at the distal end and keeps the degree of opening while in use. Compared with the clip 10 having the two holding members 12 and 13 separated from each other at the proximal end parts of the curved parts B, the clip of this type can spread wide at the distal ends of the holding parts D, which facilitates the holding of a target site not only at the distal sides of the holding parts D but in the entire areas of the holding parts D.

To ensure the longitudinal length of the holding parts D, the proximal end of the curved part 12B of the holding member 12 should preferably be in contact with the proximal end of the curved part 13B of the holding member 13.

The holding members 12 and 13 are formed of a band-shaped member having a thickness of 0.1 mm or more and 0.5 mm or less, for example. The holding members 12 and 13 may be formed by bending the band-shaped member or by preparing individual band-shaped members for the base end parts A, the curved parts B, and the holding parts D and joining the members by laser welding, for example.

As shown in FIG. 1, the holding members 12 and 13 may symmetrically be formed with respect to the long axis of the clip body 11. This enables the holding members 12 and 13 to timely come close to each other, which facilitates the holding of a target site.

As shown in FIG. 1, the holding members 12 and 13 may have substantially the same length in the longitudinal direction. The two holding members 12 and 13 come close to each other mainly at the distal ends of the holding parts D. The holding member 12 may be longer than the holding member 13 in the longitudinal direction (not shown). In this case, the two holding members 12 and 13 come close to each other not only at the distal ends of the holding parts D but also at positions proximal to the distal ends of the holding parts D, which enables the holding of a target site in all the longitudinal area of the clip body 11.

The size of the clip 10 is not limited, however, for the purpose of withdrawing the clip 10 through the forceps channel of an endoscope or together with removed matter after operation, the width of the clip body 11 is generally 0.3 mm or more and 4 mm or less and the longitudinal length of the clip body 11 in a closed state is generally 5 mm or more and 12 mm or less.

To make the holding members 12 and 13 easily deformable to facilitate the holding of a target site, the holding members, especially the holding parts D, may have an opening (not shown). More preferably, the opening is formed in the holding parts D of the holding members 12 and 13. The shape of the opening is not limited, however, the direction of the major axis of the opening may be parallel to the longitudinal direction of the clip body 11, for example.

The size of the opening is not limited, however, the length of the opening may be 30% or more and 80% or less of the maximal longitudinal length of the holding parts D and the maximal width of the opening may be 10% or more and 80% or less of the maximal width of the holding parts D, for example.

To enhance the strength of the holding members 12 and 13, the holding members 12 and 13 may be embossed to have ridges or grooves (not shown). The holding members 12 and 13 should preferably have ridges or grooves at least in the holding parts D, and more preferably in the holding parts D and the curved parts B.

The ridges or grooves may be formed integrally with the holding members 12 and 13 or as separate parts to be jointed with the holding members 12 and 13. When the ridges or grooves are formed integrally, the ridges on one main surface of the holding members 12 and 13 function as the grooves in the other main surface of the holding members 12 and 13. The ridges or grooves should preferably be formed along the axial direction of the holding members 12 and 13. The size of the ridges or grooves may be determined as the size of the above openings is.

In the longitudinal direction of the clip body 11, a length of the tightening member 15 is preferably 4% to 30% of that of the clip body 11 in a closing state. Since the length of the clip body 11 in the longitudinal direction is approximately 12 mm, for example, the length of the tightening member 15 in the longitudinal direction can be determined as 1 mm or more and 3 mm or less, for example.

The tightening member 15 may be a single ring-shaped member (shown in FIG. 1) or a ring-shaped member (not shown) formed of a wound wire rod in the form of a coil. The shape of the tightening member 15 is a circular ring shape or a polygonal ring shape, for example. The tightening member 15 may be closed in the circumferential direction, or open in the circumferential direction to have a C-shaped cross section perpendicular to the axial direction, for example.

The outer diameter of the tightening member 15 should preferably be larger than the inner diameter of the inner tubular body 40. This enables the proximal end of the tightening member 15 to come into contact with the distal end of the inner tubular body 40 when the line member 30 is pulled in the proximal direction, so that only the clip body 11 is pulled into the inner tubular body 40. As a result, the tightening member 15 moves to the distal side of the clip body 11 to close the clip 10.

The clip body 11 and the tightening member 15 may be composed of a metal material or elastic material. The clip body 11 and the tightening member 15 should preferably have a biocompatibility. The clip body 11 and the tightening member 15 are preferably composed of a Ni—Ti alloy or a stainless steel such as SUS303, SUS304, SUS631, for example. However, the clip body 11 and the tightening member 15 may be composed of the same material or the different material.

(5) Handle

The present invention also includes the medical clip device 1 including a first handle 61 connected to a proximal side of the inner tubular body 40 and being movable in an axial direction with respect to the outer tubular body 50 and a second handle 62 connected to a proximal side of the line member 30 and being movable in an axial direction with respect to the outer tubular body 50.

In FIGS. 12 and 13, the first handle 61 is disposed at the most proximal side and the second handle 62 is disposed adjacent to the first handle 61. As the first handle 61 is moved in the proximal direction with respect to the outer tubular body 50, the inner tubular body 40 moves in the proximal direction. As the second handle 62 is moved in the proximal direction with respect to the outer tubular body 50, the line member 30 moves in the proximal direction. In this way, the first handle 61 facilitates the moving operation of the inner tubular body 40 and the second handle 62 facilitates the moving operation of the line member 30.

As shown in FIGS. 12 and 13, the first handle 61 should preferably be connected with the second handle 62 via an elastic member R63. As the second handle 62 is moved in the proximal direction, the elastic member 63 made of a coil spring is compressed in the proximal direction to accumulate elastic energy. The restoring force of the coil spring helps the second handle 62 to return in the distal direction.

The first handle 61 and the second handle 62 may be composed of synthetic resin such as ABS, polycarbonate, or formed plastic such as polyurethane foam.

3. Method for Producing a Medical Clip Device

A method for producing a medical clip device 1 including steps of: preparing a line member 30; a clip 10 including a clip body 11 that has two holding members 12 and 13 facing each other and that has an engaging part J formed at a proximal side and a holding part D formed at a distal side for holding a target site, and a ring-shaped tightening member 15 attached to the clip body 11; and a connector 20 including a through hole 21 whose depth direction is nonparallel to an axial direction, and a thin part that is formed at least at a part distal to the through hole 21 and is thinner than a distal end of the through hole 21; and engaging the engaging part J with the through hole 21. The method for producing the medical clip device 1 of the present invention facilitates the connection of the clip 10 with the connector 20 by the step of engaging the engaging parts J of the clip body 11 in the through hole 21 of the connector 20.

The method for producing the medical clip device 1 will be described in detail. The medical clip device 1 includes the constituent components described in the above section "1. Connector" and "2. Medical clip device" in this specification.

The line member 30, the clip 10 including the clip body 11 and the clip 15, and the connector 20 to be required for producing the clip device 1 are prepared (step S11). The clip body 11 has two holding members 12 and 13 facing each other, has the engaging parts J (12J and 13J) at the proximal side and holding parts D at the distal side for holding a target site. The tightening member 15 is a ring-shaped member that is provided to the clip body 11. The connector 20 includes a through hole 21 whose depth direction is nonparallel to an axial direction at the distal side, and a thin part that is formed at least at a part distal to the through hole 21, and is thinner than a distal end of the through hole 21.

The inner tubular body 40 that places the line member 30 and the connector 20 at an inner lumen of the inner tubular body 40, the outer tubular body 50 that provides the inner tubular body at an inner lumen of the outer tubular body 50, and the handle for opening or closing the clip 10 are prepared (step S12). The handle includes a first handle 61 connected to the inner tubular body 40 and the second handle 62 connected to the line member 30.

The tightening member 15 whose outer diameter is larger than an inner diameter of the inner tubular body 40 and that is movable in an axial direction is attached to an outer side of the clip body 11 (step S13).

The connector 20 is connected to a distal side of the line member 30 (step S14). Specifically, the distal side of the line member 30 should preferably be connected to a hollow part 26 that is located at a proximal side of the connector 20. The connector 20 is connected to the line member 30 by this step, which facilitates the connection of the clip 10 with the line member 30 via the connector 20. As described above, the connector 20 can be connected to the line member 30 by welding such as using laser, bonding using brazing.

A proximal end part of the inner tubular body 40 is secured to the first handle 61 (step S15). The inner tubular body 40 can be secured to the first handle 61 by mechanical securing such as fitting, using screws, or caulking, bonding using adhesives such as polyurethane adhesives, epoxy adhesives, cyano adhesives, or silicone adhesives.

The outer tubular body 50 may be provided outside the inner tubular body 40 as needed. To facilitate the operation of moving the outer tubular body 50 in the longitudinal direction to the inner tubular body 40, a grip part may be provided outside the outer tubular body 50.

The line member 30 connected to the connector 20 is inserted into the inner tubular body 40 from the distal side of the inner tubular body 40, and the proximal end part of the line member 30 is secured to the second handle 62 (step S16). The line member 30 can be secured to the second handle 62 by mechanical securing such as fitting, using screws, or caulking, welding such as using laser or brazing, bonding using adhesives such as polyurethane adhesives, epoxy adhesives, cyano adhesives, or silicone adhesives, as the inner tubular body 40 is connected with the first handle 61. The second handle 62 is movable in the longitudinal direction of the inner tubular body 40 with respect to the first handle 61.

The engaging parts J that are formed at a proximal side of the clip body 11 is engaged with the through hole 21 in the connector 20 (step S17). Specifically, the connector 20 is moved toward the clip body 11 in the distal direction and then the distal end part of the connector 20 is pushed into the proximal end part of the clip body 11 so that a thin part of the connector 20, which is thinner than the distal end of the through hole 21, is disposed between the two holding members 12 and 13. As a result, the engaging parts J of the clip body 11 are engaged with the through hole 21 in the connector 20, which produces the medical clip device 1 in which the clip body 11 and the connector 20 are connected. In this way, the method for producing the medical clip device 1 of the present invention facilitates the connection of the clip body 11 with the line member 30 via the connector 20 by only engaging the engaging parts J of the clip body 11 with the through hole 21 in the connector 20.

This application claims the benefit of the priority date of Japanese patent applications No. 2015-247414 filed on Dec. 18, 2015. All of the contents of the Japanese patent applications No. 2015-247414 filed on Dec. 18, 2015, are incorporated by reference herein.

REFERENCE SIGNS LIST

1: a medical clip device
10: a clip
11: a clip body
12 and 13: a holding member
D: a holding part
J, 12J and 13J: an engaging part
14: a reinforcing member
15: a tightening member
20: a connector
21: a through hole
22: a guide part
23: an opening section
23A: a first major surface
23B: a second major surface
26: a hollow part
27: a direction adjusting part
30: a line member
40: an inner tubular body
50: an outer tubular body
61: a first handle
62: a second handle
63: an elastic member

The invention claimed is:

1. A medical clip device comprising:
an outer tubular body;
an inner tubular body provided in the outer tubular body;
a line member placed in the inner tubular body;
a clip including
   a clip body that is disposed at a distal side of the inner tubular body and has two holding members facing each other, and
   a ring-shaped tightening member that is provided to the clip body; and
a connector including
   a through hole whose depth direction is nonparallel to an axial direction,
   a thin part that is provided at least at a part distal to the through hole and is thinner than a distal end of the through hole, and
   a connecting part connected to the line member at a proximal side; wherein
a holding part for holding a target site is provided at a distal side of the clip body,
two engaging parts facing each other are formed at a proximal side of the clip body,
the engaging parts are capable of engaging with the through hole of the connector,
each of the engaging parts is formed on an inner surface of the clip body, and
the engaging parts are capable of engaging with the same through hole of the connector.

2. The medical clip device according to claim 1, wherein the engaging parts are formed at a proximal end of the clip body.

3. The medical clip device according to claim 1, wherein a minimum diameter of the through hole of the connector is larger than a maximum width of the engaging parts.

4. The medical clip device according to claim 1, wherein a distance between the two engaging parts is shorter than a depth of the through hole.

5. The medical clip device according to claim 1, wherein each of the engaging parts is projected inward in a radial direction parallel to an opening-and-closing direction of the clip body.

6. The medical clip device according to claim 1, wherein the connector has only said through hole as a through hole.

7. The medical clip device according to claim 1, wherein the connector is disposed between the holding members in an opening-and-closing direction of the clip body.

8. The medical clip device according to claim 1, wherein the engaging parts directly engage with the through hole of the connector.

9. A method for producing a medical clip device comprising steps of:
providing i) an outer tubular body, ii) an inner tubular body provided in the outer tubular body, iii) a line member placed in the inner tubular body, iv) a clip including a clip body that is disposed at a distal side of the inner tubular body and has two holding members facing each other, and a ring-shaped tightening member that is provided to the clip body, and vi) a connector including a through hole whose depth direction is nonparallel to an axial direction, a thin part that is provided at least at a part distal to the through hole and is thinner than a distal end of the through hole, and a connecting part connectable to the line member at a proximal side; wherein
a holding part for holding a target site is provided at a distal side of the clip body,
two engaging parts facing each other are formed at a proximal side of the clip body,
the engaging parts are capable of engaging with the through hole of the connector, and
each of the engaging parts is formed on an inner surface of the clip body; and
engaging the engaging parts of the clip with the same through hole of the connector.

10. The method for producing a medical clip device according to claim 9, further comprising the step of
connecting the connector to a distal side of the line member.

11. A medical clip device comprising:
an outer tubular body;
an inner tubular body provided in the outer tubular body;
a line member placed in the inner tubular body;
a clip including
   a clip body that is disposed at a distal side of the inner tubular body and has two holding members facing each other, and
   a ring-shaped tightening member that is provided to the clip body; and
a connector including
   a through hole whose depth direction is nonparallel to an axial direction,
   a thin part that is provided at least at a part distal to the through hole and is thinner than a distal end of the through hole, and
   a connecting part connected to the line member at a proximal side; wherein
the clip body has at a distal side a holding part for holding a target site, the clip body has at a proximal side two engaging parts for engaging the clip body with the connector, the two engaging parts each project inwardly from the clip body so that the two engaging parts face each other, and the thin part of the connector is disposed between the two engaging parts so that the two engaging parts detachably and directly engage with the through hole of the connector.

12. The medical clip device according to claim 1, wherein an inner wall is provided at a distal side of the through hole so that the through hole is closed.

* * * * *